(12) United States Patent
Borzatta et al.

(10) Patent No.: US 8,357,803 B2
(45) Date of Patent: Jan. 22, 2013

(54) PROCESS FOR THE PREPARATION OF 2,3,4,9-TETRAHYDRO-1H-β-CARBOLIN-3-CARBOXYLIC ACID ESTERS

(75) Inventors: Valerio Borzatta, Bologna (IT); Dina Scarpi, Florence (IT); Antonio Guarna, Serravezza (IT); Ernesto G. Occhiato, Florence (IT)

(73) Assignee: Endura S.p.A., Bologna (IT)

( * ) Notice: Subject to any disclaimer, the term of this patent is extended or adjusted under 35 U.S.C. 154(b) by 154 days.

(21) Appl. No.: 12/867,019

(22) PCT Filed: Feb. 20, 2009

(86) PCT No.: PCT/EP2009/052037
§ 371 (c)(1),
(2), (4) Date: Aug. 10, 2010

(87) PCT Pub. No.: WO2009/103787
PCT Pub. Date: Aug. 27, 2009

(65) Prior Publication Data
US 2010/0324294 A1    Dec. 23, 2010

(30) Foreign Application Priority Data

Feb. 22, 2008  (IT) ............... MI2008A0285

(51) Int. Cl.
*C07D 471/04* (2006.01)
(52) U.S. Cl. ........................................ 546/85
(58) Field of Classification Search .................. None
See application file for complete search history.

(56) References Cited

FOREIGN PATENT DOCUMENTS

| WO | WO 9519978 A1 * | 7/1995 |
|---|---|---|
| WO | WO2004011463 | 2/2004 |
| WO | WO 2007100387 A2 * | 9/2007 |

OTHER PUBLICATIONS

Zhang et al.; Improved Synthesis of Tadalafil; Organic Preparations and Procedures International; vol. 37, No. 1 (2005); p. 99-102.
Xiao-Xin Shi et al.; "Highly stereoselective Pictet-Spengler reaction of D-tryptophan methyl ester with piperonal: convenient syntheses of Cialis (Tadalafil), 12a-epi-Cialis, and their deuterated analogues"; Tetrahedron Asymmetry, vol. 19, p. 435-442 (2008).
Notification of Transmittal of the International Preliminary Report on Patentability dated Jun. 11, 2010 for International Application No. PCT/EP2009/052037.
Tomas Herraiz; L-Tryptophan Reacts with Naturally Occurring and Food-Occurring Phenolic Aldehydes to Give Phenolic Tetrahydro-β-carboline Alkaloids: Activity as Antioxidants and Free Radical Scavengers; Journal of Agriculture and Food Chemistry, 2003, 51, 2168-2173.
Maria L. Lopez-Rodriguez; Stereospecificity in the Reaction of Tetrahydro-β-carboline-3-carboxylic Acids with Isocyanates and Isothiocyanates. Kinetic vs. Thermodynamic Control; J. Org. Chem., 1994, 59, 1583-1585.

* cited by examiner

*Primary Examiner* — Janet Andres
*Assistant Examiner* — Timothy R Rozof
(74) *Attorney, Agent, or Firm* — Abelman, Frayne & Schwab

(57) ABSTRACT

The present invention relates to the process of preparation of 2,3,4,9-tetrahydro-1/−/-β-carbolin-3-carboxylic acid esters substituted in position 1 of the general formula (I). in the preferred diastereoisomeric form through a single step starting from tryptophan in racemic form and/or its enantiomers and from 3,4-(methylenedioxy)benzaldehyde.

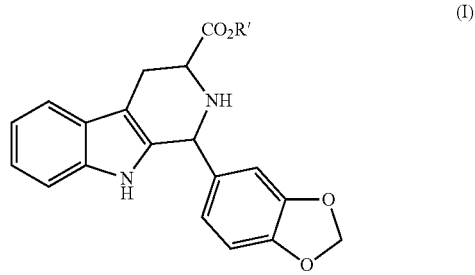

12 Claims, No Drawings

PROCESS FOR THE PREPARATION OF 2,3,4,9-TETRAHYDRO-1H-β-CARBOLIN-3-CARBOXYLIC ACID ESTERS

FIELD OF THE INVENTION

The present invention relates to the synthesis process of 2,3,4,9-tetrahydro-1H-β-carbolin-3-carboxylic acid esters substituted in position 1.

PRIOR ART

The compounds of the formula (I)

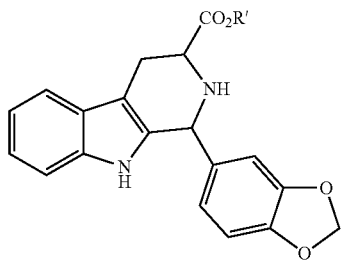

are extensively used in the synthesis of active ingredients such as alkaloids and drugs. The most well-known intermediate is represented by methyl ester of 2,3,4,9-tetrahydro-1-(3,4-benzodioxolyl)-β-carbolin-3-carboxylic acid in the diastereoisomeric cis form, used in the synthesis of the drug (6R,12aR)-2,3,6,7,12,12a-esahydro-2-methyl-6-(3,4-methylendioxyphenyl)-pyrazin-[2',1':6,1]pyrido[3,4-b]indol-1,4-dione, also known as Taladafil.

The compounds of the general formula (I) have two stereogenic centres where the substituents different than hydrogen atoms at the asymmetric carbon atoms can be in cis or trans configuration. It is well known that biological active compounds containing at least one asymmetric carbon atom have different biological activity depending on their stereoisomerism, being one stereoisomer more active than the other one.

It is known that the products of the general formula (I) in the suitable configuration cis or trans can be obtained by means of Pictet-Spengler reaction between tryptophan in the suitable configuration D or L and 3,4-(methylendioxy)-benzaldehyde, as described here below:

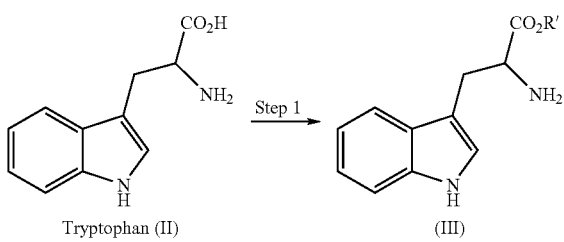

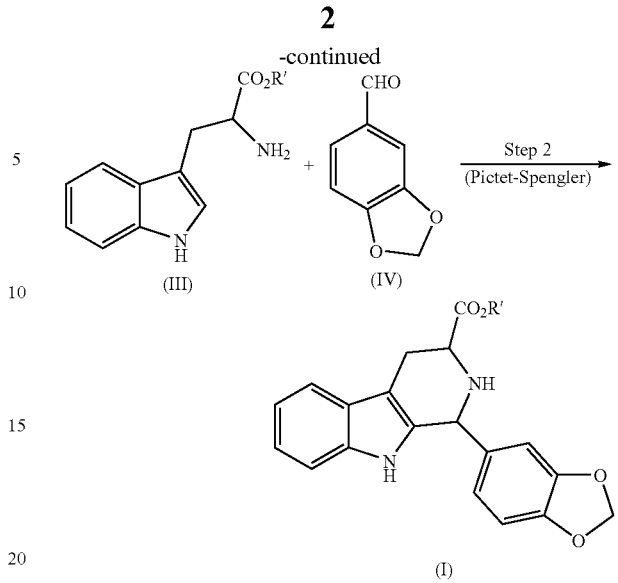

In particular, it is extensively described the synthesis of the methyl ester of cis 2,3,4,9-tetrahydro-1-(3,4-benzodioxolyl)-β-carbolin-3-carboxylic acid, intermediate for the production of Taladafil.

U.S. Pat. No. 5,859,006 describes the synthesis of Taladafil and of its intermediate methyl ester of cis 2,3,4,9-tetrahydro-1-(3,4-benzodioxolyl)-β-carbolin-3-carboxylic acid by reaction between D-tryptophan methyl ester and 3,4-benzodioxole-1-carbaldehyde (piperonal) in dichloromethane and in the presence of trifluoroacetic acid.

In this case both the diastereoisomers are obtained and the cis isomer is separated from trans isomer by preparative chromatography. The above described process has the disadvantage of the chromatographic separation, the usage of the highly corrosive trifluoroacetic acid, long reaction times (4-5 days) and low yields in cis isomer (37-42%).

In the patent application WO2004/011463 the synthesis of Taladafil and of the methyl ester of cis 2,3,4,9-tetrahydro-1-(3,4-benzodioxolyl)-β-carbolin-3-carboxylic acid is reported by reaction between D-tryptophan methyl ester hydrochloride, and piperonal in anhydrous isopropyl alcohol.

The process has the disadvantage of using anhydrous isopropyl alcohol being thus of scarce industrial applicability. In the patent application WO2005/068464 is described a preparation process where D-tryptophan methyl ester and piperonal are condensed in the presence of trifluoroacetic acid, in a suitable solvent and in the presence of molecular sieves to adsorb water released during the reaction. Both cis and trans diastereoisomers are obtained which, by treatment with aqueous hydrochloric acid, give the hydrochloride salt of the cis isomer, that precipitates in the reaction media and subsequently is isolated and reacted with the suitable reactants to give Taladafil. The above described process has the disadvantage of using molecular sieves, difficult to be exploited in an industrial scale, and the fact that the reaction is carried out in two steps requiring intermediates isolation.

In U.S. Pat. No. 6,143,746 is described a process of preparation where D-tryptophan methyl ester and piperonal are condensed in the presence of trifluoroacetic acid in anhydrous dichloromethane. Trans isomer is obtained by solvent concentration and filtration. The mother liquid, containing mainly cis isomer, is further concentrated and the cis isomer is obtained by crystallization adding isopropyl ether as co-solvent. The above described process has the disadvantage of using a chlorinated solvent, an extremely corrosive acid as trifluoroacetic acid, long reaction times and separation by fractioned crystallization.

In U.S. Pat. No. 6,143,757 is described a process for the preparation of Taladafil starting from D-tryptophan methyl ester hydrochloride, by Pictet-Spengler reaction in the presence of chlorinated solvents, trifluoroacetic acid and piperonal, giving the methyl ester of 2,3,4,9-tetrahydro-1-(3,4-benzodioxolyl)-β-carbolin-3-carboxylic acid in the diastereoisomeric forms cis and trans. The cis form is then separated by preparative chromatography and the so obtained diastereoisomer is reacted with the proper isocyanate to give Taladafil. The above described process has the disadvantage of using trifluoroacetic acid, highly corrosive, and the need of separating the two diastereoisomers by preparative chromatography.

In the patent application WO2006/110893 is described a process to obtain Taladafil and its precursor, the methyl ester of cis 2,3,4,9-tetrahydro-1-(3,4-benzodioxolyl)-β-carbolin-3-carboxylic acid. The latest is obtained by reaction of D-tryptophan methyl ester and/or its suitable salt in a solvent chosen among alkyl esters of carboxylic acids such as, for example, ethyl acetate in the presence of trifluoroacetic acid, at room temperature or at 50° C. for long reaction times (7 days). The cis diastereoisomer is then obtained by filtration with a yield variable between 32% and 75%. The described process presents the disadvantage of using the highly corrosive trifluoroacetic acid and long reaction times (7 days).

In the patent application US2006/0258865 is described a process to obtain Taladafil and its precursor cis 2,3,4,9-tetrahydro-1-(3,4-benzodioxolyl)-β-carbolin-3-carboxylic acid methyl ester. The latest is prepared by reaction of D-tryptophan methyl ester hydrochloride with piperonal in an aprotic dipolar solvent with a high boiling point such as N,N-dimethyl acetamide (DMA) in the presence of a dehydrating agent such as anhydrous sodium sulfate in considerable quantities and by heating for 30-35 hours. The so-obtained diastereoisomeric mixture is then treated under heating with aqueous hydrochloric acid for further 6-10 hours in order to epimerize the trans diastereoisomer and the cis isomer is separated by crystallization from a mixture toluene/cyclohexane after organic extraction of the acid aqueous solution. The above described process has, by the way, the disadvantage of using an aprotic dipolar solvent having a high boiling point as DMA, which is difficult to recover and a chemical dehydrating agent such as sodium sulfate in considerable quantities, followed by reaction with hydrochloric acid to obtain cis isomer and final crystallization after extraction of the aqueous acid solution.

In Herraiz T. et al., J. Agric. Food Chemistry, 2003, 51, 2168-2173, L-tryptophan is reacted with the suitable aldehyde to give the correspondent tetrahydro-β-carbolin-3-carboxylic acid in a diastereoisomeric mixture in the presence of sulfuric acid for long reaction times (9 days). By using this method starting directly from the amino-acid, the obtained product is represented by carbolin-carboxylic acid only and not by its ester. Moreover the reaction is carried out with long times without separation of different diastereoisomers.

In Lopez-Rodriguez M. et al., J. Org. Chem. 1994, 59, 1583-1585, is described a process to obtain the suitable 2,3,4,9-tetrahydro-1H-β-carbolin-3-carboxylic acid substituted in position 1 by reacting L-tryptophan and benzaldehyde in diluted sulfuric acid for 7 hours. Such a product, obtained in racemic form, was then used in the following reaction with isocyanate or isothiocyanate. Nothing was reported about obtaining the carboxylic ester starting from tryptophan.

To summarize, the prior art does not report any teaching on how to obtain the appropriate diastereoisomer of 2,3,4,9-tetrahydro-1H-β-carbolin-3-carboxylic acid esters substituted in position 1 in an only reaction (one-pot reaction). In fact, it starts directly from the suitable ester of D- or L-tryptophan or, in case it starts from the correspondent amino-acid, the synthesis stops at 2,3,4,9-tetrahydro-1H-3-carbolin-3-carboxylic acid substituted in position 1.

Moreover, the preparation of the 2,3,4,9-tetrahydro-1H-β-carbolin-3-carboxylic acid ester substituted in position 1 shows several disadvantages that can be summarized in long times (days) of reaction, need of chromatographic separation, use of dehydrating agents such as molecular sieves or chemical products such as sodium sulfate, separation of the diastereoisomeric mixture and subsequent epimerization to give the desired isomer, use of anhydrous solvents.

SUMMARY

It has been found now a new process to obtain 2,3,4,9-tetrahydro-1H-β-carbolin-3-carboxylic acid esters substituted in position 1 of the formula (I)

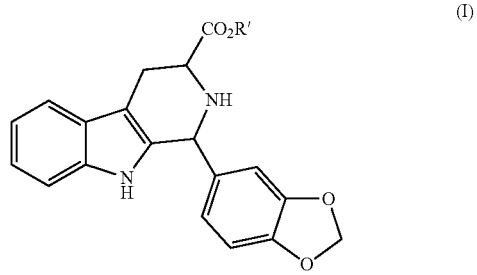

(I)

in the preferred diastereoisomeric form starting directly from tryptophan (D-, L. or racemic), an aminoacid easily available and not expensive through an one pot reaction with 3,4-(methylenedioxy)benzaldehyde (piperonal) in a suitable alcoholic solvent and in the presence of a protic acid. In the mentioned formula (I), R' represents alkyl, cycloalkyl, cycloalkyl containing heteroatoms, aryl, aralkyl, heteroaryl or heteroaralkyl substituent.

Preferably in R', the alkyl and aralkyl substituents are $C_1$-$C_8$ alkyl e $C_1$-$C_8$ aralkyl; the cycloalkyl substituent is represented by 3-8 member rings; the substituents containing heteroatoms are represented by 4-8 member rings containing 1 to 3 heteroatoms chosen among O, N, S; moreover all the cyclic substituents can be optionally substituted, in particular, by $C_1$-$C_8$ alkyl, hydroxyl, $C_1$-$C_8$ alkoxy, nitro, halogen groups.

It is an object of the present invention a process to obtain in an only synthesis step the product (I) starting from tryptophan (II) in acid catalysis conditions as reported in Scheme 1:

Scheme 1

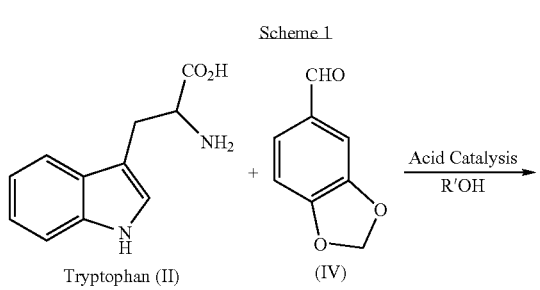

Tryptophan (II)   (IV)

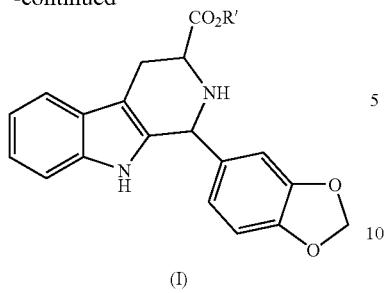

(I)

The reaction is carried out in the suitable alcoholic solvent R'OH (giving R' group) in the presence of an inorganic protic acid in excess relative to the stechiometric amount, that's relative to the tryptophan (II) moles. Preferably the protic acid is used in an excess till to 50% relative to the tryptophan (II) moles; an excess between 5% and 30% is preferred; an excess between 10% and 30% is more preferred.

In the process shown in scheme 1 two reactions together are involved in the same reactor without any separation of the intermediates The first one is the addition of the aldehyde (IV) to position 2 of the indolic ring of tryptophan (II) with subsequent closure of the piperidinic ring (Pictet.Spengler reaction); the second one is the esterification of $CO_2H$ group.

The process uses an inorganic acid easily available, low cost, industrially applicable and no difficult handling such as, for example hydrochloric acid. Moreover the process allows the preparation of the ester of the 2,3,4,9-tetrahydro-1H-β-carbolin-3-carboxylic acid substituted in position 1 in accordance with the preferred diastereoisomeric form through in situ conversion of the no desired diasteroisomeric form to the desired one.

DETAILED DESCRIPTION OF THE INVENTION

In the process of the present invention, the starting material tryptophan (II) can be used in racemic form, in enantiomeric enriched form or in enantiomeric pure form (L- or D-).

The preferred molar ratio between tryptophan (II) and the compound (IV) (3,4-(methylenedioxy)benzaldehyde) is between 0.8 and 1.5; the more preferred molar ratio is between 0.9 and 1.3; the even more preferred molar ratio is between 0.9 and 1.1; a particularly preferred molar ratio is 1.0.

The inorganic protic acid is chosen among hydrochloric acid, sulfuric acid, nitric acid. Hydrochloric acid and sulfuric acid are preferred; hydrochloric acid is particularly preferred. Hydrochloric acid means the aqueous solution of concentrated hydrochloric acid, being the concentration of said hydrochloric acid between 30% and 37% (% w/w). A concentration between 33% and 37% (% w/w) is preferred; a concentration of 37% (% w/w) is particularly preferred.

The molar ratio between the protic acid (e.g. hydrochloric acid) and tryptophan (II) is between 1.0 and 1.5; the preferred molar ratio is between 1.05 and 1.3; the molar ratio between 1.1 and 1.2 is particularly preferred.

The solvent R'OH is chosen on the basis of the substituent R' to be introduced in the compound (I). Illustrative but non-limiting examples are methanol, ethanol, n-propanol, isopropanol, n-butanol and its isomers, n-pentanol and its isomers, n-hexanol and its isomers n-heptanol and its isomers, n-octanol and its isomers, cyclopentanol, cyclohexanol, cycloheptanol, hydroxypiperidine, phenyl alcohol, benzyl alcohol, methylbenzyl alcohol, 4-methoxybenzyl alcohol, 3-methoxybenzyl alcohol, 2-methoxybenzyl alcohol. 4-nitrobenzyl alcohol, tetrahydrofuranemethanol.

Methanol, ethanol, n-propanol, isopropanol, n-butanol, sec-butanol, isobutanol are preferred; methanol is particularly preferred.

The reaction is carried out at the temperature of reflux of the solvent for a time preferably between 12 and 36 hours, for example 24 hours. During the reaction, water is formed, giving a variation of the boiling point of the pure solvent; the formed hydroalcoholic solution is distilled off and the reaction solution is conveniently added with further fresh R'OH solvent till the solvent boiling point is maintained.

At the end of the reaction, the mixture is evaporated under vacuum, suitably into the same reaction vessel, recovering the racemic and raw compound (I) as a solid. From this compound (I) the single and pure diastereoisomers cis and/or trans can be recovered by chromatography or by using other systems known to separate diastereoisomers, if needed, coming previously by the appropriate epimerization reactions to increase the yield in the desired diastereoisomeric form.

In accordance with a preferred procedure of said epimerization, the raw solid compound (I) is treated with a diluted aqueous solution of hydrochloric acid, heated to a temperature between 40° C. and 70° C., for example between 50° C. and 60° C. fur further 40-100 hours, for example 60-80 hours. The hydrochloric acid is used in a molar excess (relative to the starting tryptophan (II)) between 5% and 50%, preferably between 5% and 30%, more preferably between 10% and 20%. The obtained precipitate is the hydrochloric salt of the compound (I) in the cis diastereoisomeric configuration and is separated by filtration, washed with a suitable alcoholic or ethereal solvent such as, for example, isopropanol or isopropyl ether and dried.

The mother liquids after the precipitation of the hydrochloric salt contain a residue of the cis-compound (I) in solution, the remaining part of the compound (I) as trans form, small amounts of the same compounds as not ester forms and possible small amounts of no reacted aldehyde (IV) or tryptophan (I). These mother liquids can be conveniently treated in accordance with known systems to recover these products.

In particular, the aldehyde (IV) can be recovered from the mother liquids by extraction with an organic solvent, for example ethyl or isopropyl ether; the compounds of the formula (I) can be recovered by precipitation with a suitable base (for example $NaHCO_3$); the recovered compounds can be recycled in a subsequent Pictet-Spengler, esterification and epimerization (recycle) to enrich them again in the desired enantiomeric form and to recover further amounts of said enantiomeric form.

Some illustrative, but non limiting examples of the present invention are described below

EXPERIMENTAL PART

Example 1

To a suspension of D-tryptophan (10.20 g; 50.0 mm) in methanol (45 ml), an aqueous solution of HCl 37% (5 ml) is added.

Piperonal (7.50 g; 50.0 mm) is then added to the resulting solution, which is allowed to react at reflux temperature for 25 hrs. The solvent is removed by distillation and continuously replaced with fresh methanol up to a volume of 400 ml. of the distilled in total. After the solvent evaporation, an aqueous solution of HCl 0.3M (183 ml) is added to the residue and the so-obtained solution is kept at 55° C. for 72 hrs. The precipitate is filtered, washed with diisopropyl ether and dried under vacuum to give the cis ester hydrochloride (10.79 g; 27.82 mm) with a yield of 56%. The aqueous solution is washed with diisopropyl ether (2×90 ml) to recover the un-reacted piperonal and neutralized with solid NaHCO$_3$ (6.80 g). The resulting precipitate is filtered, washed with diisopropyl ether and dried under vacuum to give a solid residue (6.18 g). The solid recovered from the aqueous layer is analysed by chromatography and resulted in having, the following composition:

cis ester (1.90 g; 5.41 mm); trans ester (1.45 g; 4.13 mm); cis acid (1.58 g; 4.68 mm); trans acid (1.25 g; 3.71 mm).

The total yield of the process is 92% (total yield as esters: 75%; total yield as cis ester 67%)

$^1$H NMR (200 MHz, DMSO-d6) δ (ppm): 10.84 (s, NH, 1H), 7.54 (d, J 6.7 Hz, 1H), 7.29 (d, J 7.4 Hz, 1H), 7.17-6.99 (m, 5H), 6.10 (s, OCH$_2$O, 2H), 5.87 (s br, CHAr, 1H), 4.73 (s br, CHCO$_2$CH$_3$, 1H), 3.84 (s, CO$_2$CH$_3$, 3H), 3.38-3.26 (m, CH$_2$CHCO$_2$CH$_3$, 2H).

$^{13}$C NMR (50.33 MHz, DMSO-d6) δ (ppm): 168.5 (s), 148.5 (s), 147.1 (s), 136.7 (s), 128.9 (s), 127.0 (s), 125.4 (s), 125.0 (d), 122.0 (d), 119.2 (d), 118.2 (d), 111.6 (d), 110.4 (d), 108.3 (d), 106.3 (s), 101.5 (t), 57.6 (d), 55.2 (d), 53.0 (q), 22.2 (t).

Example 2

To a suspension of the solid residue recovered as described in example 1 (6.18 g) and D-tryptophan (10.20 g; 50.0 mm) in methanol (61 ml), HCl 37% (6.6 ml) is added. Piperonal (7.50 g; 50.0 mm) is added to the resulting solution, which was allowed to react at reflux temperature for 25 hrs. The solvent is removed by distillation and continuously replaced with fresh methanol up to a volume of 680 ml. of the distilled in total.

After solvent evaporation an aqueous solution of HCl 0.3 M (183 ml) is added to the residue and the so-obtained solution is kept at 55° C. for 72 hrs. The precipitate is filtered, washed with diisopropyl ether and dried under vacuum to give the cis ester hydrochloride (12.90 g; 33.26 mm) with a yield of 66.7%.

The aqueous solution is washed with diisopropyl ether (2×90 ml) to recover the un-reacted piperonal and neutralized with NaHCO$_3$ (9.10 g). The resulting precipitate is filtered, washed with diisopropyl ether and dried under vacuum to give a solid residue (10.60 g).

The precipitate is analyzed by chromatography and resulted having the following composition:

cis ester (2.58 g; 7.34 mm); trans ester (2.36 g; 6.72 mm); cis acid (3.09 g; 9.16 mm); trans acid (2.55 g; 7.59 mm).

Total yield in cis ester: 81.4%

The invention claimed is:

1. Process for the preparation of the compounds of the formula (I)

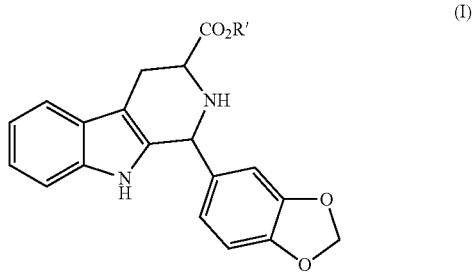

comprising the reaction between tryptophan and 3,4-(methylenedioxy)benzaldehyde in an alcoholic solvent of the formula R'OH in the presence of a molar excess, relative to tryptophan, of a inorganic protic acid, where in R'OH and in the formula (I), R' represents a same substituent chosen among alkyl, cycloalkyl, cycloalkyl containing heteroatoms, aryl, heteroaryl or aralkyl.

2. Process according to claim 1 wherein tryptophan is D-tryptophan, L-tryptophan or their mixtures.

3. Process according to claim 1 or 2, wherein the acid is hydrochloric acid, sulfuric acid or nitric acid.

4. Process according to claim 1, wherein the protic acid is present in molar excess up to 50% relative to tryptophan.

5. Process according to claim 4, wherein the protic acid is present in a molar excess between 5% and 30% relative to tryptophan.

6. Process according to claim 5, wherein the protic acid is present in molar excess between 10% and 30% relative to tryptophan.

7. Process according to claim 1, wherein tryptophan and 3,4-(methylenedioxy)benzaldehyde are used in equimolar amounts.

8. Process according to claim 1, wherein the solvent R'OH is selected from the group consisting of methanol, ethanol, n-propanol, isopropanol, n-butanol and its isomers, n-pentanol and its isomers, n-hexanol and its isomers, n-heptanol and its isomers, n-octanol and its isomers, cyclopentanol, cyclohexanol, cycloheptanol, hydroxypiperidine, phenyl alcohol, benzyl alcohol, methylbenzyl alcohol, 4-methoxybenzyl alcohol, 3-methoxybenzyl alcohol, 2-methoxybenzyl alcohol, 4-nitrobenzyl alcohol, tetrahydrofuranemethanol.

9. Process according to claim 1, wherein the reaction among tryptophan, 3,4-(methylenedioxy)benzaldehyde and R'OH is carried out at reflux temperature of R'OH, for a time between 12 and 36 hours.

10. Process according to claim 1, wherein the obtained product (I) is subsequently submitted to an epimerization reaction to increase the enrichment in one of its diastereoisomers.

11. Process according to claim 10, wherein the diastereoisomer is the cis diastereoisomer.

12. Process according to claim 11, wherein the epimerization is carried out by reacting the compound (I) at a temperature between 40°-70° C. for a time between 40 and 100 hours, with a molar excess of aqueous hydrochloric acid relative to the starting tryptophan.

* * * * *

UNITED STATES PATENT AND TRADEMARK OFFICE
CERTIFICATE OF CORRECTION

PATENT NO. : 8,357,803 B2
APPLICATION NO. : 12/867019
DATED : January 22, 2013
INVENTOR(S) : Valerio Borzatta et al.

It is certified that error appears in the above-identified patent and that said Letters Patent is hereby corrected as shown below:

On the Title page Item (73) Assignee should read: Endura S.p.A., Bologna (IT)
    Università degli Studi di Firenze, Firenze (IT)

Signed and Sealed this
Twenty-fourth Day of September, 2013

Teresa Stanek Rea
*Deputy Director of the United States Patent and Trademark Office*